(12) United States Patent
Dubrul et al.

(10) Patent No.: US 6,221,006 B1
(45) Date of Patent: Apr. 24, 2001

(54) ENTRAPPING APPARATUS AND METHOD FOR USE

(75) Inventors: William Richard Dubrul, Redwood City, CA (US); Richard E Fulton, Grand Junction, CO (US)

(73) Assignee: Artemis Medical Inc., San Mateo, CA (US)

( * ) Notice: Subject to any disclaimer, the term of this patent is extended or adjusted under 35 U.S.C. 154(b) by 0 days.

(21) Appl. No.: 09/248,088

(22) Filed: Feb. 9, 1999

Related U.S. Application Data

(60) Provisional application No. 60/074,199, filed on Feb. 10, 1998, and provisional application No. 60/105,284, filed on Oct. 22, 1998.

(51) Int. Cl.$^7$ ................................................ A61B 17/22
(52) U.S. Cl. ............................................. 600/159; 606/117
(58) Field of Search ................................. 606/159, 158, 606/160, 113, 114, 115, 127, 128, 200

(56) References Cited

U.S. PATENT DOCUMENTS

| | | | |
|---|---|---|---|
| 2,816,552 | 12/1957 | Hoffman | 128/305 |
| 3,320,957 | 5/1967 | Sokolik | 128/311 |
| 3,996,938 | 12/1976 | Clark, III | 128/348 |
| 4,469,100 | 9/1984 | Hardwick | 128/328 |
| 4,611,594 * | 9/1986 | Grayhack et al. | 128/328 |
| 4,650,466 | 3/1987 | Luther | 604/95 |
| 4,799,495 | 1/1989 | Hawkins et al. | 128/754 |
| 4,807,626 * | 2/1989 | McGirr | 128/328 |
| 4,852,568 | 8/1989 | Kensey | 128/325 |
| 4,907,572 | 3/1990 | Borodulin et al. | 606/128 |
| 4,986,279 | 1/1991 | O'Neill | 128/754 |
| 4,996,583 | 2/1991 | Debbas | 604/98 |
| 5,030,201 * | 7/1991 | Palestrant | 604/22 |
| 5,031,634 | 7/1991 | Simon | 128/754 |
| 5,059,197 | 10/1991 | Urie et al. | 606/116 |
| 5,102,415 * | 4/1992 | Guenther et al. | 606/159 |
| 5,158,565 | 10/1992 | Marcadis et al. | 606/185 |
| 5,183,463 | 2/1993 | Debbas | 604/98 |
| 5,195,533 | 3/1993 | Chen et al. | 128/754 |
| 5,221,269 | 6/1993 | Miller et al. | 604/281 |
| 5,330,483 | 7/1994 | Heaven et al. | 606/114 |
| 5,336,191 | 8/1994 | Davis et al. | 604/165 |
| 5,365,943 | 11/1994 | Jansen | 128/772 |
| 5,382,259 | 1/1995 | Phelps et al. | 606/151 |
| 5,383,892 | 1/1995 | Cardon et al. | 606/198 |
| 5,396,897 | 3/1995 | Jain et al. | 128/748 |
| 5,466,225 | 11/1995 | Davis et al. | 604/165 |
| 5,487,392 | 1/1996 | Haaga . | |
| 5,507,769 | 4/1996 | Marin et al. | 606/198 |
| 5,527,276 | 6/1996 | Bruce | 604/54 |
| 5,562,725 | 10/1996 | Schmitt et al. | 623/1 |
| 5,571,091 | 11/1996 | David et al. | 604/165 |

(List continued on next page.)

FOREIGN PATENT DOCUMENTS

| | | |
|---|---|---|
| 966 920 | 12/1999 | (EP) . |
| 983 749 | 3/2000 | (EP) . |
| 2020557 | 11/1979 | (GB) . |
| WO 97/20504 | 6/1997 | (WO) . |
| WO 98/08441 | 3/1998 | (WO) . |
| WO 99/04704 | 2/1999 | (WO) . |
| WO 99/44506 | 9/1999 | (WO) . |
| WO 00/12009 | 3/2000 | (WO) . |
| wo 00/12010 | 3/2000 | (WO) . |

*Primary Examiner*—Gary Jackson
*Assistant Examiner*—Lien Ngo
(74) *Attorney, Agent, or Firm*—James F. Hann; Haynes & Beffel LLP

(57) ABSTRACT

Medical devices that have a novel mechanical trap(s) on the distal end of a shaft that is used for the removal of material from the body. Further an expandable channel is included to entrap the material that aid with removal or obliteration of tissue or foreign bodies is disclosed.

8 Claims, 10 Drawing Sheets

U.S. PATENT DOCUMENTS

| | | | |
|---|---|---|---|
| 5,595,185 | 1/1997 | Erlich | 128/754 |
| 5,603,722 | 2/1997 | Phan et al. | 606/198 |
| 5,643,282 * | 7/1997 | Kieturakis | 606/114 |
| 5,665,092 | 9/1997 | Mangiardi et al. | 606/86 |
| 5,720,764 | 2/1998 | Naderlinger | 606/200 |
| 5,728,133 | 3/1998 | Kontos | 606/213 |
| 5,759,187 * | 6/1998 | Nakao et al. | 606/114 |
| 5,769,816 | 6/1998 | Barbut et al. | 604/96 |
| 5,792,157 * | 8/1998 | Mische et al. | 606/159 |
| 5,795,308 | 8/1998 | Russin | 600/567 |
| 5,800,409 | 9/1998 | Bruce | 604/280 |
| 5,800,445 | 9/1998 | Ratcliff et al. | 606/116 |
| 5,807,276 | 9/1998 | Russin . | |
| 5,810,744 | 9/1998 | Chu et al. | 600/567 |
| 5,810,849 | 9/1998 | Kontos | 606/144 |
| 5,814,064 | 9/1998 | Daniel et al. | 606/200 |
| 5,827,312 | 10/1998 | Brown et al. | 606/167 |
| 5,827,324 * | 10/1998 | Cassell et al. | 606/200 |
| 5,855,585 | 1/1999 | Kontos | 606/144 |
| 5,857,464 * | 1/1999 | Desai | 128/658 |
| 5,868,708 * | 2/1999 | Hart et al. | 604/104 |
| 5,876,411 | 3/1999 | Kontos | 606/144 |
| 5,879,357 | 3/1999 | Heaton et al. | 606/110 |
| 5,916,145 | 6/1999 | Chu et al. | 600/121 |
| 5,928,260 | 7/1999 | Chin et al. | 606/200 |
| 5,928,261 | 7/1999 | Ruiz | 606/200 |
| 6,027,520 * | 2/2000 | Tsugita | 606/200 |
| 6,053,876 | 4/2000 | Fisher | 600/562 |

* cited by examiner

ENTRAPPING APPARATUS AND METHOD FOR USE

CROSS REFERENCE TO RELATED APPLICATIONS

The present invention claims the benefit of (a) Provisional Patent application Ser. No. 60/074,199 filed Feb. 10, 1998, and (b) Provisional Patent application Ser. No. 60/105,284 filed Oct. 22, 1998, the full disclosures are incorporated herein by reference.

FIELD OF THE INVENTION

In general, this invention relates to medical devices and methods. In particular, the instant invention relates to an improved device for the removal of tissue or foreign bodies from the body. One particular use of this improved device is removal of obstructions from the tubular channels of the body. These obstructions are usually blood clots (thrombi) or other byproducts of occlusive vascular disease (e.g. plaque) or even instruments/implants lost by the physician during an intervention including but not limited to wires, stents, staples, components, embolic coils, etc. Further, the removal of matter from non-vascular channels is disclosed. Even further, the instant invention can be used for the removal of tissue including but not limited to tissue biopsies, cancerous, necrotic, infected, or other diseased tissue from solid or semi-solid tissue.

BACKGROUND OF THE INVENTION

Occlusive vascular disease is a common ailment in people resulting in enormous costs to the health care system. Blood clots are the most common type of occlusion. Removal of clots from the body has been studied for several years and many techniques (devices and methods) have been studied and practiced. One of the more common techniques is one referred to as embolectomy. Embolectomy is a treatment whereby the clot is removed from the body as opposed to being dissolved and then reabsorbed. Another alternative is thrombolysis. As the name indicates, this is lysing (eating) of the thrombus (blood clot). Usually this requires a significant amount of potentially dangerous and always expensive drug that is injected into the vasculature. The drug delivery is sometimes aided with special catheters, which may increase efficacy, but certainly increase cost. The deposit of sinuous plaque (arteriosclerosis) to the inner wall of arteries usually precedes clot formation. Several expensive devices (dilatation balloons, stents, mechanical cutters, etc.) have been introduced to fight this vascular occlusive disease, but none of which has proven to be the 'magic bullet' to treat this ubiquitous disease. Because of the various problems with all of the techniques and approaches to solving this medical condition, there exists no particular method or device that is considered the most accepted mode of treatment.

Unfortunately, cancer too is a common ailment resulting in over 1,500 deaths every day in the U.S. (550,000 every year). Therapy modalities for cancer are plentiful and continued to be researched with vigor. Still, the preferred treatment continues to be physical removal of the cancer. When applicable, surgical removal is preferred (breast, colon, brain, lung, kidney, etc.). Surgical removal is often extremely invasive and efforts to remove cancerous tissue in a less invasive way continue, but have not yet been perfected. The only cure for cancer continues to be early diagnosis and subsequent early treatment. As cancer therapies continue at an earlier stage of diagnosis, the cancerous tissue is smaller and smaller. Early removal of these smaller cancers demand new techniques for removal and obliteration that are less invasive. The instant invention describes new devices for less invasive cancer therapy. There are many techniques and devices known in the art for removing blockages in the vascular system and other passageways of the human body as well as removing other diseased tissue.

There is a continuing need for improved devices to meet at least the following objectives.

The first objective is to reduce cost. This is particularly important in recent years where it is clear for safety and sanitary reasons that these will be single use devices. A device, even though it performs a function in some improved manner, will not be widely used if it is considerably more costly than the alternatives available.

A second objective is to provide a device that is simple to use and in a very real sense simple to understand. This will encourage its adoption and use by medical personnel. It will also tend to keep cost low.

The third objective is to provide a device that entails a procedure with which the medical profession is familiar so that the skills that have been learned from previous experience will continue to have applicability.

A fourth objective relates to the effectiveness and thoroughness with which the biological tissue or foreign body is removed. With regard to biological tissue removal, it is important that an optimum amount of the mater be removed; recognizing that no device is likely to provide one hundred percent optimization.

A fifth objective concerns safety, a matter which is often so critical as to trump the other considerations. It is important to avoid unnecessary tissue trauma. In the case of using the present invention or its similar inventions in the tubular channels of the body, it is critically important to avoid breaking up matter in a fashion that leads to flushing elements of the blockage throughout the body involved. The same may be true for removal of diseased tissue removal, certainly in the case of removal of cancerous tissue.

There are trade-offs in design considerations to achieve the above five interrelated objectives. Extreme simplicity and a very simple procedure might overly compromise safety. Addressing all of these considerations calls for some trade-off between the objectives.

Accordingly, a major object of this invention is to provide an improved removal device that achieves the objectives of reduced cost, enhanced simplicity, a standard procedure, high effectiveness and a high degree of safety. Most particularly, it is an object of this invention to achieve these objectives with an enhanced trade-off value for the combined objectives.

For these reasons, it is desirable to provide an improved device that may circumvent some of the problems associated with previous techniques. This improved medical device provides a new configuration that will eliminate some of those problems and methods for their use, which facilitate removal of vascular obstructions in the operating room or interventional suite.

BRIEF DESCRIPTION

In brief, one embodiment of this invention is particularly adapted to the removal of blockages in vascular channels (biologic or synthetic) of the body. That embodiment combines an expanding channel catheter and a support wire having an occlusion-engaging element.

The support wire may extend through the expandable channel device or catheter, through or around the occlusion and at its distal end has an annular braided element attached thereto. The support wire is a dual element support wire having a core and an annular shell that slides on the core. The distal end of the core is attached to the distal end of the annular braided element and the distal end of the shell is attached to the proximal end of the annular braided element. Thus movement of the core and shell relative to one another moves the braided element from a radially retracted position which is useful for insertion through the catheter to a radially expanded position which expands it to the sidewall of the channel. When the annular braided element is in its radially compressed (smaller diameter) state, it can be passed through or around the occlusion together with the rest of the wire to reside on the distal end of the occlusion. When the braided element is expanded and moved proximally (that is, in a retrograde fashion), it will engage the occlusion and force the occlusion into the catheter. Alternatively, no motion of the engaging element may be required if aspiration is applied. In this case, the engaging expandable channel device acts as a seal to prevent the suction from aspiration to remove much material beyond its point of deployment in the channel. Further, no motion of the distal engaging element is required if the expandable engaging element is moved distally toward the occlusion and thusly engulfs the obstruction by its forward motion and expandability.

The distal end of the catheter is proximal of the occlusion and contains an expandable blocking mechanism that extends radially from the distal end of the catheter to the wall of the graft or body passageway. This catheter expandable blocking element also has a radially retracted insertion state and a radially expanded blocking state. The expandable blocking element is similar in construction to the distal engaging element in that it is a tubular braid, which may or may not be covered by or integrated with a thin film or membrane.

This distal tubular braid of expandable channel device is usually bonded to the distal end of the catheter or an integral part of the catheter. Pushing the assembly forward where it will meet resistance to the obstruction actuates the expandable characteristic of the expandable engaging element. Alternatively, there may be a mandril or drawstring that may cause the tubular braid to expand. In this case, the distal blocking element is expanded in a similar fashion. In this radially expanded state, the expandable engaging element and its film (if desired) blocks the annulus around the catheter so that the occluded blood or other obstruction which is being removed is forced into the catheter where it is aspirated, obliterated or otherwise removed.

The instant invention also describes another use of the same device of the instant invention with minor changes. In this case, the expandable tubular braid may be used as a tissue removal device as opposed to an obstruction removal device. In other words, the instant invention could be used for harvesting vein grafts, removal of plaque from arteries taking biopsy samples, or removal of diseased tissue (i.e. cancerous or other disease) from solid or semi-solid tissue. In this case, the present invention would be pushed forward and when it reached an expanded diameter (either by design of the tubular braid, design of the entire expandable assembly or by tissue constraints) it would separate tissue via the wall of the expanded tubular device. This separation of tissue may be aided by other energy sources such as, but not limited to mechanical (cutting), thermal, electrical energies, etc. Once the desired amount of tissue is removed, the expandable tubular braid (with tissue remaining within its inner diameter) may be removed from the body. This removal may include pulling the expanded tubular braid element and thus putting it into a tensile configuration, where the tubular braided element will have a tendency to be elongated and consequently the diameter of the expanded device may be decreased depending upon the matter contained within as well as the physical constraints put on the device by its particular environment within the body.

SUMMARY OF THE INVENTION

The instant invention provides an improved device of the type having a shaft with a proximal end and a distal end. The improvement comprises configuring at least a distal portion of the shaft so that it can assume a shape(s) along its shaft (proximally, mid-section or distally) that will act as a TRAP or dragger. In the case of body channels or cavities, this trap mechanism(s) is moved along the lumen (artery, vein, intestine, stent, graft, or other hollow vessel or organ) and then past the obstruction or tissue (clot, plaque, or other obstruction). Once it is past the obstruction, the user (physician/technician) can actuate the trap mechanism(s) so that it is enlarged beyond its original size/diameter and aid in removing the obstruction using another novel, elongate expandable channel. This novel, expandable channel has the ability to start small but is easily enlarged when the obstruction or tissue meets the distal end of the device. Once the material located in at least the distal end of this expandable channel (and possibly farther into it) the expandable channel that is distal to the material may shrink down to the original diameter or close to it. In other words, this new channel acts like a snake swallowing a large piece of food that originally is larger than the snake's throat or intestines. For that reason, this new channel will be referred to as PYTHON. This technique may be aided with other aids such as the addition of lytic agents, monoclonal antibodies, vibration, irrigation, aspiration, therapeutic ultrasound or other energies such as mechanical, electrical, magnetic, etc. or pharmaceutical therapy(s) that will aid with removal or obliteration of the material. MIS (Minimally Invasive Surgery) or LIS (Least Invasive Surgery) devices described herein such as catheters and guide wires, for example are the most common tools used by least invasive interventionalists today. These devices are available in a variety of shapes and sizes from 0.008–0.500" diameters and from 6.0–80.0" in length. In other respects, the catheters and guide wires or other device (s) of the instant invention will have the geometries, characteristics, and dimensions of those commonly employed for the intended purpose (e.g. introduction to a blood vessel (LIS) or surgical tissue removal (MIS). MIS and LIS are often interchanged in their usage. Usually LIS refers to catheters, guide wires, (and the like) that are used within the body, often within the channels of the body. MIS typically refers to videoscopic surgery where miniature cameras are used to accomplish surgery. However, because of the large crossover of the use of these terms, the inventors do not wish to limit the scope of the devices described herein when these terms are used.

DESCRIPTION OF THE BACKGROUND ART

The intellectual property regarding vascular obstruction removal is extensive. Some of the pertinent embolectomy and atherectomy descriptions are set forth in a number of issued U.S. patents, including U.S. Pat. Nos. 5,498,236, 5,380,273 and 5,713,848 by the inventor of the instant invention (Dubrul) as well as U.S. Pat. Nos. 4,762,130, 5,827,729, 5,476,450, 4,998,919, 5,772,674, 5,370,653, 5,733,294, 4,762,130, 5,443,454, 5,419,774, 5,112,347, 4,030,503, 5,653,684 and 3,978,863.

U.S. Pat. Nos. 5,498,236, 5,380,273 and 5,713,848 by the inventor of the instant invention (Dubrul) describe a Motion Catheter that is used for 'the removal and dissolution of obstructions within the lumens of the body'. In these issued patents, Dubrul et al additioaally discloses a filter/occluder that is similar to the TRAP mechanism disclosed heretofore. However, Dubrul describes the filter occluder specially to keep particulate (e.g. emboli) from travelling downstream and causing deleterious effects on the patient (e.g. stroke). U.S. Pat. No. 4,762,130 by Fogarty describes a spiral balloon for the removal of blood clots (thrombus). U.S. Pat. No. 5,653,684 describes a device that uses and expandable tubular braid on the distal end of a catheter, but with this device the inventor uses the device to crack atheromous plaque using radio frequency energy.

The intellectual property regarding cancer therapies and removal is extensive as well. Some of the pertinent cancer therapy descriptions are set forth in a number of issued U.S. patents, including U.S. Pat. Nos. 5,368,597, 5,769,794, 5,647,372, 5,465,731 and 5,443,472.

U.S. Pat. No. 5,368,597 describes a reclosable pouch retaining tissue. U.S. Pat. No. 5,769,794 discloses a bag for cancerous tissue removal. U.S. Pat. No. 5,647,372 describes a specimen retrieval pouch. U.S. Pat. No. 5,465,731 discloses a method and device for specimen retrieval. U.S. Pat. No. 5,443,472 describes a morcellator system for diseased tissue.

Further, the pending patent application by the inventor (Dubrul et al) of the instant invention, Ser. No. 60/074,183, is pertinent to the instant invention with regard to using the distal TRAP mechanisms as a Anchor and Tensioner as well as a Detachable Vessel Occluder.

Further U.S. Pat. No. 5,827,729 by Auth describes an aspiration thrombectomy catheter with an angled distal end to allow aspiration of blood clot into the catheter. Ruggio, in U.S. Pat. No. 5,476,450, discloses an apparatus for aspirating substances into a catheter also. U.S. Pat. No. 4,998,919 describes a catheter designed to infuse a lytic agent and aspirate the residual clot through a larger lumen. U.S. Pat. No. 5,772,674 describes a thrombectomy device, which includes a delivery and receiving catheter having balloons at their distal ends. In addition, Cragg, in U.S. Pat. No. 5,370,653, describes a thrombectomy device with rotating brushes.

BRIEF DESCRIPTION OF THE FIGURES

FIG. 3 illustrates the TRAP of the instant invention where tubular braid is used. Not illustrated is a covering that may be over or within the expandable TRAP.

FIG. 7A shows a treatment mechanism of the instant invention as well.

In FIG. 8A, the PYTHON is in its un-deployed state.

DESCRIPTION OF THE EXEMPLARY EMBODIMENTS

Figure 1:
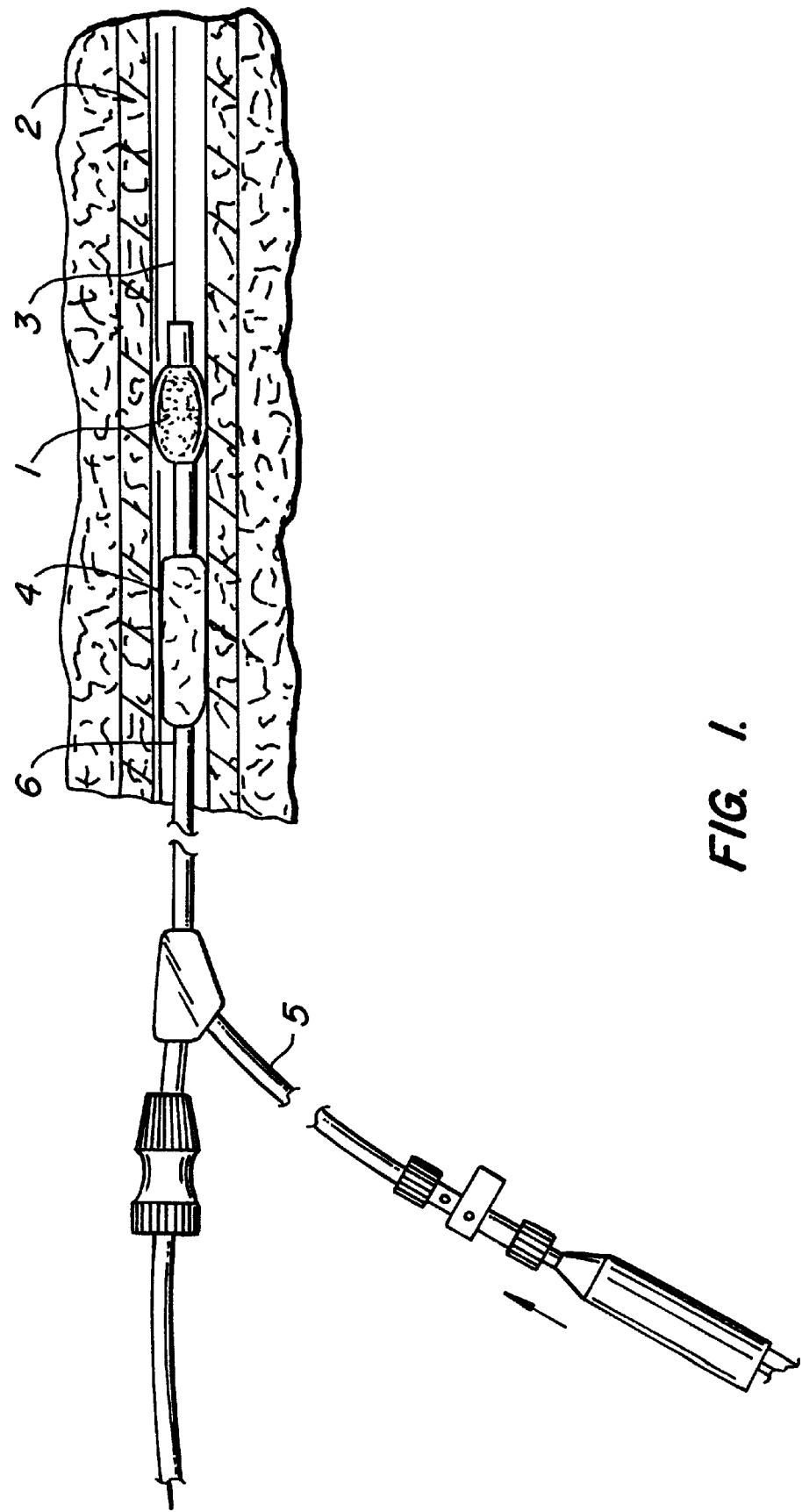
FIG. 1 is a cross sectional view of a preferred embodiment of the instant invention, being an inflatable balloon with a roughened surface or covering. This is one preferred embodiment of the TRAP as disclosed herein.

FIG. 1 is a cross sectional drawing showing the device of this invention fully deployed in an occluded channel 2. The FIG. 1 drawing shows the TRAP element at the distal end of the catheter in its radially expanded state. It is important to note that the TRAP element may take a variety of shapes as would be required for the particular application. The preferred shape is likely to be an ovoid shape. FIG. 1 is an illustration of the TRAP device using an inflatable balloon 1. FIG. 1 shows the balloon in its deployed or inflated condition while in position in a tubular channel 2 that is occluded with a thrombus 4. Hence FIG. 1 is an artery or vein 2 and the obstruction 4 is a blood clot. However, the obstruction could be different from a blood clot as described earlier and the tubular channel could be different from a vein or artery. The balloon catheter/TRAP 6 has been inserted into the vessel 2 via a guidewire 3. The balloon is inflated with balloon inflation line 5. Not illustrated in FIG. 1 is the expandable channel of the present invention that is illustrated in FIGS. 4, 5, 6, 7, 8 & 9. In FIG. 1, the balloon has a roughened surface or covering to aid with removal of the clot 4 (or other material) from its adhesion to the wall of the vessel 2.

Figure 2A:
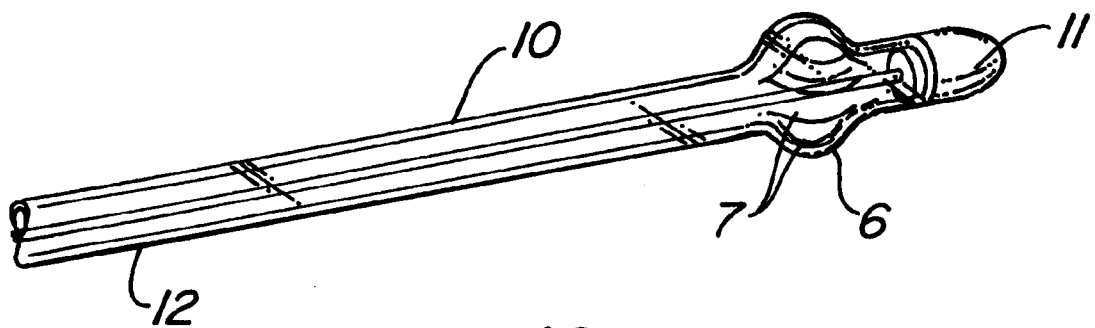
FIG. 2A is a schematic view of the preferred embodiment of the instant invention and an alternative design of the TRAP described herein.
Figure 2B:
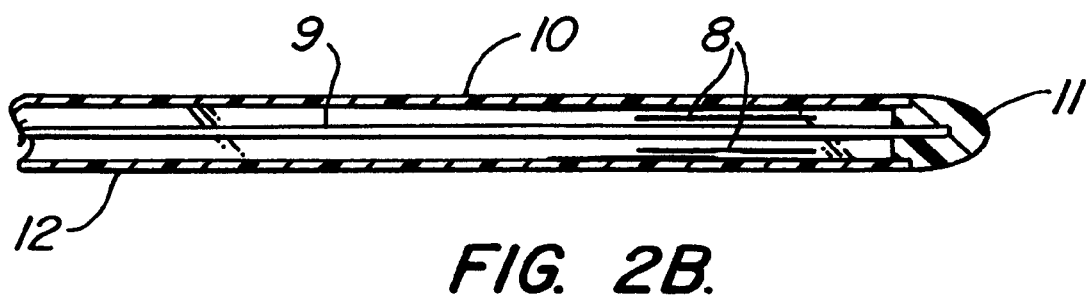
FIG. 2B shows a malecot type TRAP with a roughened surface.
Figure 2C:
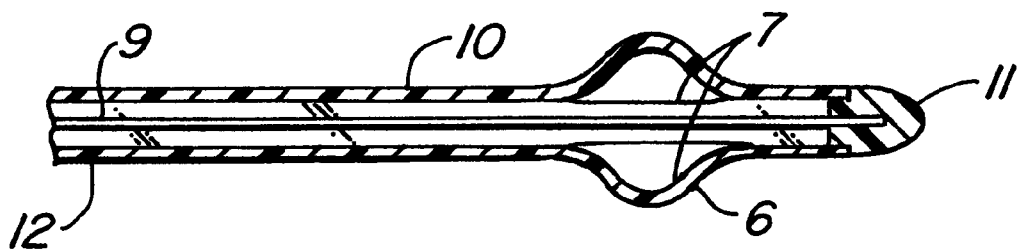
FIG. 2C is a cross sectional view of the malecot style TRAP of the instant invention in its un-deployed state. Not illustrated in FIGS. 2A, 2B & 2C is a covering, membrane, or film that could be used over or within the ribs or wings of the malecot style TRAP. Further, other mechanisms to change the rigidity of the mechanism are not illustrated.

Turning now to FIGS. 2A–2C, a preferred embodiment of the Entrapping Device. FIG. 2A is a schematic illustration of the TRAP 12 device with a malecot type mechanism 6 on the distal portion where the malecot has a roughened surface. The malecot is in its deployed condition. The malecot mechanism could have a covering over or within the ribs or wings, but is not illustrated in the figure. This covering could be elastic or inelastic material. Further, a membrane could be located within the malecot it self. In this case, the ribs or wings 7 of the malecot would have a membrane attached to the wings. This attachment could be the material that the wings are made of or an added material. The material used in construction of the malecot style TRAP 12 vary from a polymer to metals. If metal is used, the covering or attachment between the ribs or wings 7 would need to be a polymer such as but not limited to polyurethanes, silicone rubber, latex, polyethylenes, PET, MYLAR PEBAX etc. FIG. 2B is a cross sectional view of the malecot mechanism in its undeployed state. Longitudinal slits 8 located on the TRAP 12 allow the ribs or wings 7 to be deployed outward. There are at least two slits 8, but often four or six may be used. The slits are usually in pairs (but not necessarily) in that they are symmetrically placed around the circumference of the shaft 10. An inner mandril or tube 9 is used to deploy or un-deploy the malecot. The malecot could be programmed to be in the deployed condition in its relaxed state. In this case, the inner mandril or tube 9 would be pushed distally with respect to the shaft 10 to un-deploy the malecot. Alternatively, the mandril or tube 9 could be pulled proximally with respect to the shaft 10 when the malecot is un-deployed in its relaxed condition. The inner mandril or tube 9 would be a tube when a guide wire is used to place the TRAP 12 into position. In this case, there would be a lumen through the entire TRAP catheter 12 and an exit hole in the tip 11 of the device. The guide wire and through lumen is not illustrated here. FIG. 2C is a cross sectional illustration of the TRAP 12 with the wings 7 expanded.

Figure 3:
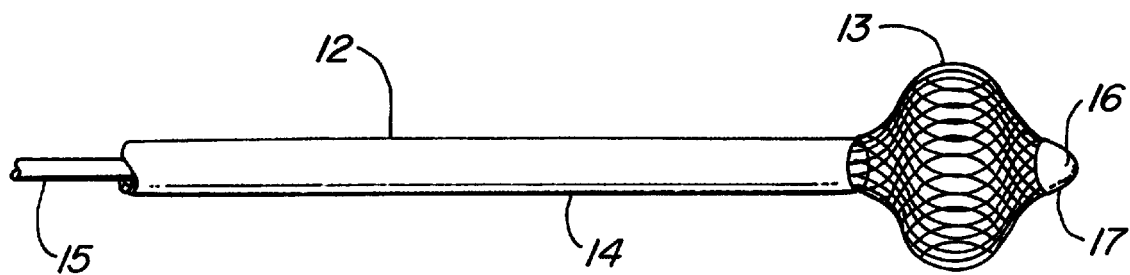
FIG. 3 is a schematic illustration of the instant invention and yet a third alternative design of the TRAP described herein.

Turning now to FIG. 3, is a preferred embodiment of the Entrapping Device, the TRAP 12. Where the radially expanding mechanism is accomplished using an expanded tubular braid on the distal portion of the device although with all of the TRAP designs disclosed herein, the location of the TRAP along the device may vary proximally and distally as required for the particular application. This braid may or may not have a covering over it within it or under it. It is important to note that the TRAP element may take a variety of shapes as would be required for the particular application. FIG. 3 is a longitudinal view of the distal portion of a support tube 14 with a braided occlusion-TRAP element 13 in its radially expanded state. This is the state where the support tube 14 and TRAP element 13 has been inserted through or around the occluding material that is to be removed. An inner wire or tube 15 is used for actuation of the braided element. The braided TRAP 13 could be expanded in its relaxed state or conversely could be in its smaller diameter, un-deployed (not shown) in its relaxed state. The tubular braid can be programmed to be expanded in its relaxed state. In this case, the inner wire or tube 15 is pushed in a distal direction to force the braided TRAP 13 into a smaller diameter and un-deployed state. The inner wire or tube 15 may be a tube when a guide wire is used. In this case, the inner tube 15 would have a lumen extending through the entire device with an exit hole 16 in the distal tip 17. In the case where the tubular braid is un-deployed and in a small diameter in its relaxed state, the inner wire or tube 15 is pulled with respect to the outer shaft 14 to actuate the TRAP 13 and radially expand it.

Figure 4A:
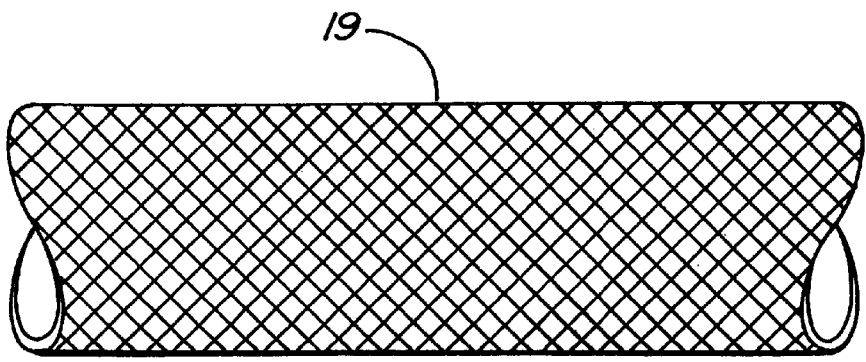
FIG. 4 illustrates the tubular braid of the instant invention. This expandable component is pertinent to the design of the expandable channel illustrated in FIGS. 5, 6, 7, 8 & 9 as well as the TRAP illustrated in FIG. 3. Not illustrated is a covering that may be over or within the expandable channel.
Figure 4B:
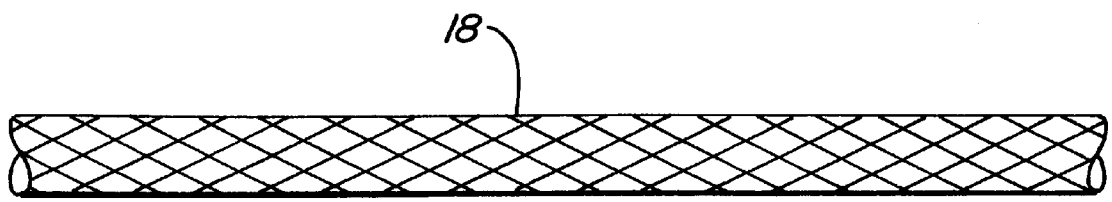

Turning now to FIG. 4, there is illustrated the tubular braid that is used in the TRAP 13 of FIG. 3 as well as the expandable channel, PYTHON, in FIGS. 5–9. FIG. 4A illustrates the tubular braid 18 in its smaller diameter. FIG. 4B illustrates the tubular braid 19 in its expanded state. Shortening the tubular braid 18 causes the expansion. This is also referred to as putting it into compression longitudinally. Significant description of this tubular braid is described later in the patent.

Figure 5:
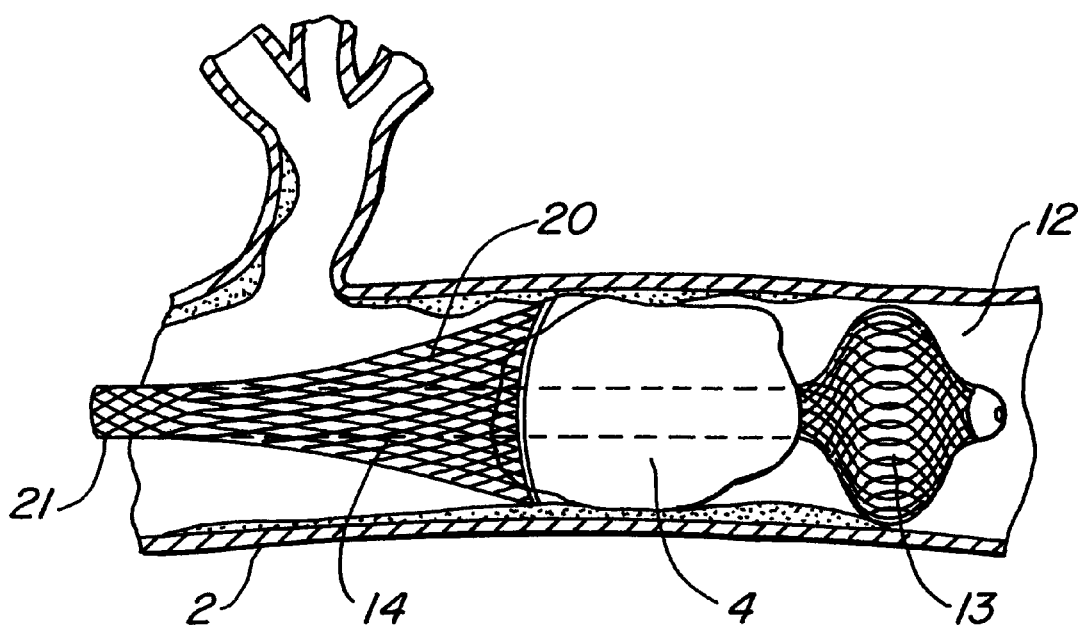
FIG. 5 illustrates the expandable channel referred to as the PYTHON in place in a tubular channel of the body in its partially deployed condition. Not illustrated is a covering that may be over or within the expandable channel.

FIG. 5 is an illustration of the PYTHON expandable channel 20 as it is beginning to open and engulf the thrombus 4 inside a vessel 2. Again FIG. 5 illustrates vascular usage for clot removal, but the instant invention described can be used in other tubular channels within the body for removal of visceral tissue as well as synthetic matter. The TRAP 12 is in its deployed and radially expanded condition distal to the material to be removed. It has been passed through or around the material in a smaller and un-deployed condition. The shaft 14 of the TRAP 12 is located inside the PYTHON 20. Usually, the TRAP 12 has been put into position and the PYTHON 21 is inserted over it in its smaller condition. In this drawing both the PYTHON 20 & 21 as well as the TRAP 13 are constructed using multi-stranded braid. The braid material can be plastic, fabric, metallic, etc.

Alternatively, although not illustrated in FIG. 5, the PYTHON 21 could be inserted into breast, liver, brain (or other solid or solid-like tissue) for removal of matter there. This is usually done via a pecutaneous (LIS (Least Invasive Surgery) or MIS (Minimally Invasive Surgery)) access site. This preferred embodiment is illustrated in FIGS. 7 & 8.

In FIG. 5, the TRAP 12 illustrated is of the braided type, but could also be any variety of TRAPS. In all figures, there may be structures (not illustrated) in the figures that increase or decrease the strength of the TRAP mechanism(s).

Figure 6:
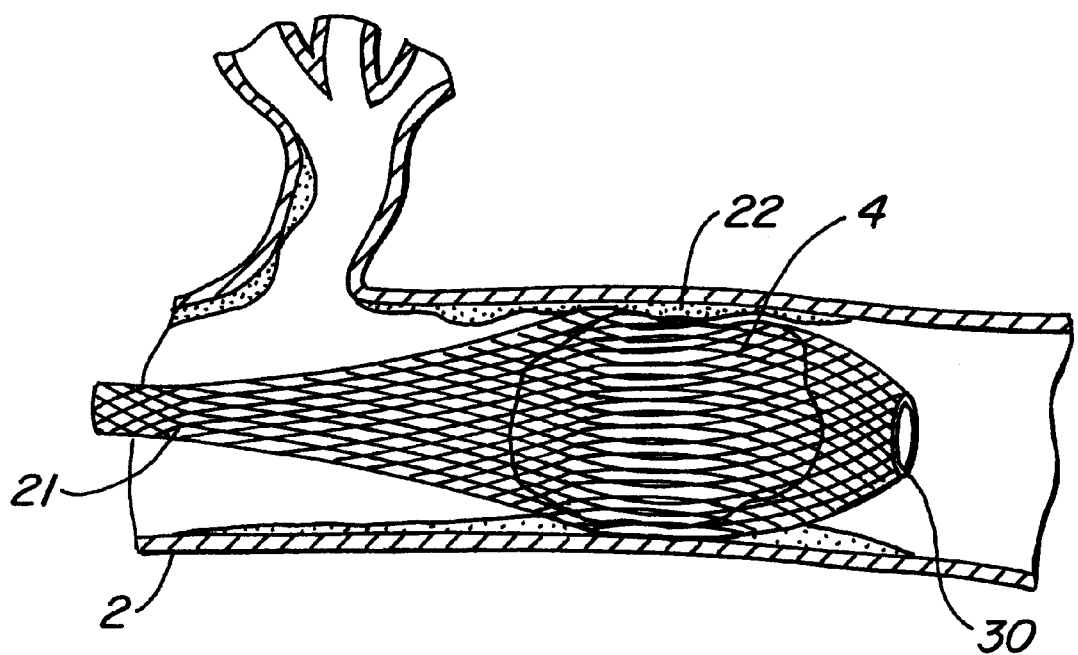
FIG. 6 illustrates the PYTHON expandable channel of the instant invention. Here the PYTHON is in its deployed condition and has engulfed material in the vessel. Not illustrated is a covering that may be over or within the expandable channel.

Turning now to FIG. 6 a preferred embodiment is illustrated where the material to be removed (blood clot) 4 is fully encapsulated inside the PYTHON expandable channel 22 and ready for removal, dissolution or other obliteration. In FIG. 6, there is no TRAP. This is illustrated to show that potentially the system may be used without a TRAP as described earlier. Alternatively, the TRAP could be removed after entrapping the matter, but prior to its removal from the body. In this case, the TRAP 12 would be undeployed to its smaller diameter. This smaller diameter is near to the diameter of the TRAP shaft 14. In its smaller diameter, it could be withdrawn first prior to removal of the PYTHON with entrapped matter if preferred. However, it is likely that the PYTHON with entrapped matter would be withdrawn first, leaving the TRAP in place should it be desired to return to the same location again. The TRAP 12 in this instance could be used as an anchor or tensioner so that a device (i.e. catheter) could be easily placed over the shaft 14 of the TRAP 12. This is an exemplary embodiment of the instant invention and could be used without an Entrapping Device. For example it could be used anywhere, a guide wire is used. Often times the guide wire has a tendency to move after it has been placed exactly where the interventionalist has placed it. Often the time and effort to place the guide wire is the most critical of the interventional procedure and assuring that this placement is retained is very valuable.

Further, a preferred embodiment of this anchoring is the fact that the physician can also apply tension to the guide wire shaft 14 from outside the body. This is valuable because often disease in tubular channels within the body occur significant distances from the entry point accomplished by the physician. Further, the guide wire is often passed through tortuous paths along the tubular channel. These tortuous paths are difficult with a guide wire, but can be even more difficult when trying to pass another device such as, but not limited to a catheter or endoscope. By applying tension to the shaft 14 of the TRAP 12, these tortuous paths are much less difficult to cross than without said tension or anchoring applied. This is accomplished because the TRAP 12 can be made very small commensurate to conventional guide wires.

Figure 7A:
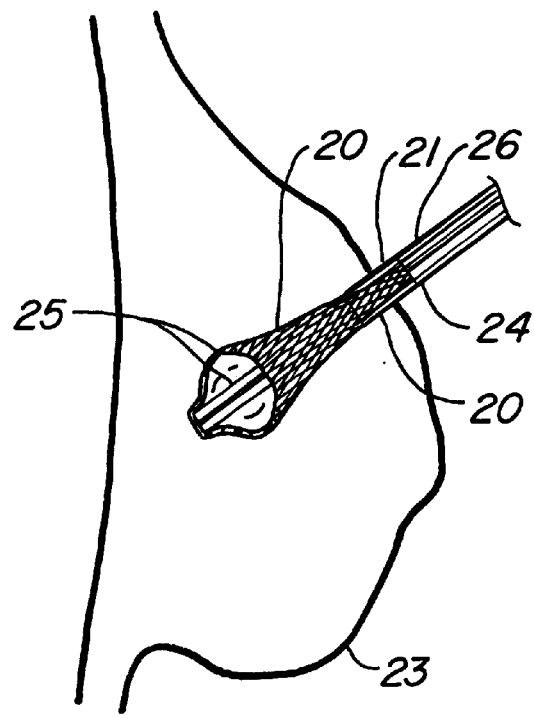
FIG. 7A illustrates the expanding channel of the instant invention in its un-deployed state as it is entering a breast for tissue removal.
Figure 7B:
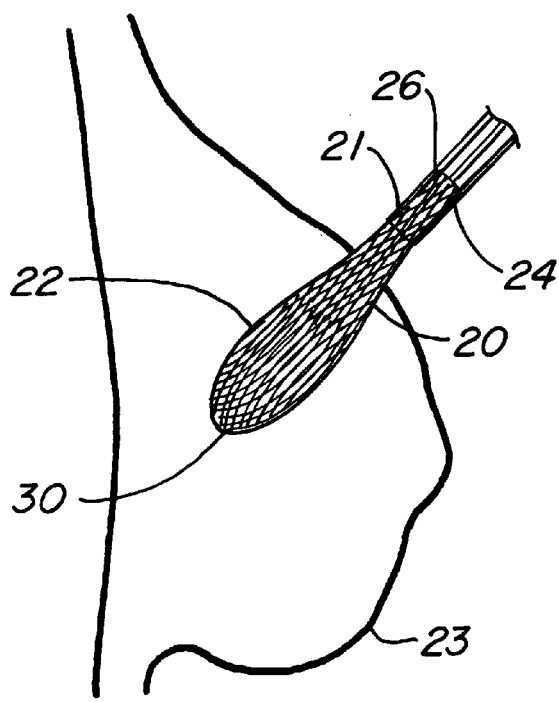
FIG. 7B illustrates the expandable channel, PYTHON, of the instant invention whereby it is deployed and has engulfed the tissue as well as the therapeutic mechanism. Not illustrated is a covering that may be over or within the expandable channel.

Referring now to FIG. 7, the preferred embodiment of the instant invention is illustrated for removing diseased tissue from the breast 23. FIG. 7A illustrates a therapeutic instrument 24 for obliteration of diseased tissue including but not limited to cancer, fibroids, etc. The instrument is placed percutaneously into the breast 23 (or other tissue including, but not limited to liver, brain, pancreas, lungs, etc.). The therapeutic instrument 24 is located in the area of the diseased tissue and activated. This therapy or activation can be a variety of therapies including but not limited to cryosurgery, electrosurgery, radio frequency, thermal energy, laser surgery, cutting, etc. The ribs or blades 25 are shown here in an expanded condition. They are first inserted into the breast 23 (or other tissue) in an unexpanded condition not illustrated. When they are inserted in the unexpanded condition, they approximate the smaller diameter of the shaft 26. This is readily accomplished in several ways commonly known to anyone normally skilled in the art. One such mechanism would be similar to the mechanism used to expand the TRAP described in the instant invention where an inner member is moved with respect to the shaft 26. In this case the ribs would move from a smaller diameter and flattened condition to an expanded condition as illustrated in FIGS. 7A & 7B. The expansion could also be varied by the physician in that the more relative motion of the inner member to the shaft 26, the greater the expansion of the ribs or blades. This is important because the physician can then control the amount of tissue to be treated and/or removed. The ribs or blades 25 could be one or more in number. This rib design is commonly used in expanding baskets for stone or other obstruction removal.

In the case of cutting, other energies or therapies as describe above may not be needed. In this case, the ribs or blades may be sharp so that a twisting or turning of the device 24 would accomplish severance of the tissue along the shape of the expanded blades or ribs 25. If there is one blade or rib 25, the device would be revolved 360 degrees. If two ribs or blades, 180 degrees and so on, depending upon the number of ribs or blades 25. This turning or revolving can be accomplished by the physician him or her self or could be incorporated into the device itself with the addition of a variety of different energy sources. Further, the cutting could be aided with a variety of other energy sources described above.

Once the tissue is treated by any of the above means, the ribs may help in providing a scaffold for advancing the PYTHON 20. However, the ribs or blades 25 may not be required in the situation where the PYTHON is used as a tissue removal alone without the aid of the therapeutic characteristic described herein. This is further described below in regard to FIGS. 8A & 8B.

Referring now to FIG. 7B, the PYTHON 20 has been moved forward and expanded around the treated tissue. In this case, the expanded channel 22 of the PYTHON has entrapped the distal end of the therapeutic device 24 including the ribs or blades 25 and the treated tissue within. Once entrapment is assured, the PYTHON may be aided with closing the distal end 30 utilizing a variety of mechanisms only one of which may be a snare or drawstring attached around the distal end of the PYTHON 30. Further, the PYTHON expandable channel may be covered or coated within the filaments or both with an elastic or inelastic membrane. This may be important for a number of reasons the least of which is that upon removal of the treated tissue; it may be desirable to prevent any particulate contamination of the diseased tissue from passing through the tubular braid. Without this membrane protection, diseased tissue could be left in the tract used for insertion of the system while the system is removed from the body. Certainly, this is critical when the diseased tissue is cancer and the only therapy used is that of removing it from the body as opposed to chemotherapy, cryo therapy, thermal therapy, etc. Even with these other therapies, it may be desirous to not allow the tissue being removed from the body to pass through the porous tubular braid. Upon removal, the physician usually pulls the PYTHON. This pulling puts the PYTHON expanding channel into a tensile mode which allows the PYTHON to be reduced in diameter and in some cases back to it's original smaller diameter 21.

Figure 8A:
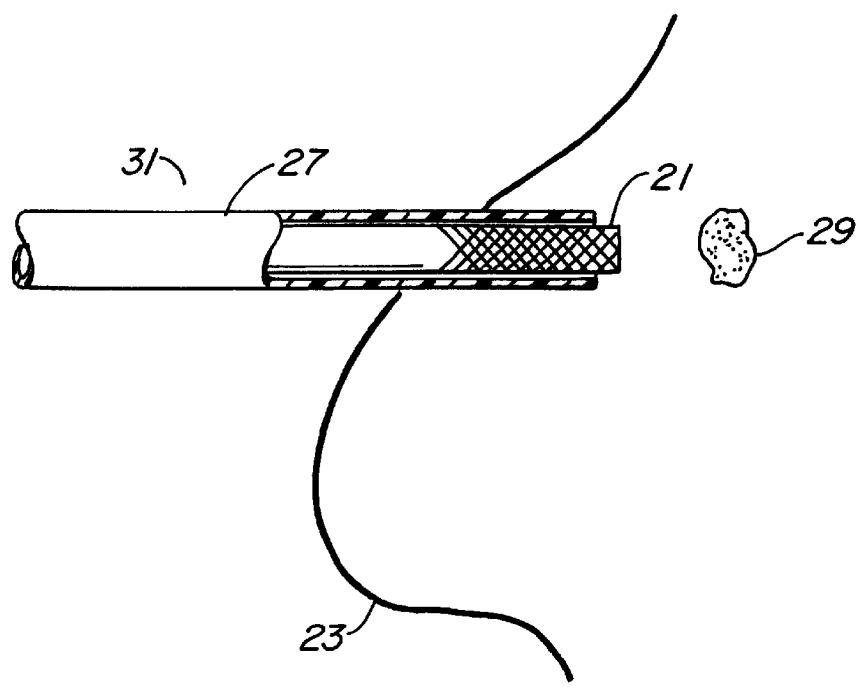
FIG. 8A illustrates the PYTHON expandable channel of the instant invention as it enters the breast.

Turning now to FIG. 8, another preferred embodiment is described. FIG. 8A illustrates a cross sectional view of the Entrapping Device 31 inserted into the breast 23. The Entrapping Device 31 is aimed at diseased tissue 29 located in the breast. The location of this diseased tissue 29 can be determined by a number of different diagnostic tools including, but not limited to MRI, x-ray, ultrasound, palpation, mammography, etc. In FIG. 8A, the un-deployed and smaller PYTHON expandable channel is constrained by an outer tube 27. This outer tube 27 has before been neither delineated nor illustrated in the figures in the aforementioned embodiments; however, it is likely that it will be used in all of them. Once the device 31 is in the appropriate position as is illustrated in FIG. 8A, the PYTHON expandable channel 21 is pushed forward. Upon pushing the PYTHON forward, it expands due to resistance felt by the tissue in front of it or other mechanism. The amount of expansion can be controlled by the design of the tubular braid, surrounding tissue characteristics or in the design of the device itself as previously described.

Figure 8B:
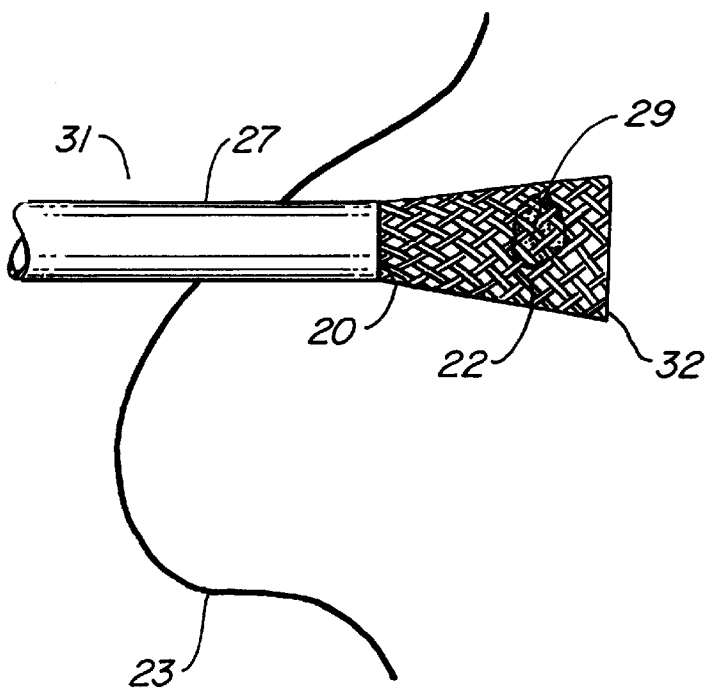
FIG. 8B illustrates the PYTHON expandable channel of the instant invention whereby the PYTHON is deployed and has engulfed the target tissue of the breast to be removed. Not illustrated is a covering that may be over or within the expandable channel.

Turning now to FIG. 8B, the PYTHON expandable channel 22 has entrapped the diseased tissue. This entrapment may be aided by adding energies including, but not limited to thermal, electrical, radio frequency, etc. or with the aid of a cutting edge on the most distal end 32 of the PYTHON expandable channel. Further, although not illustrated here, the distal end of the PYTHON expandable channel 32 may have a mechanism that will close the expanded channel prior to removal. This mechanism may include a mechanism for severing the tissue that is not severed during the pushing forward of the PYTHON as well.

Figure 9A:
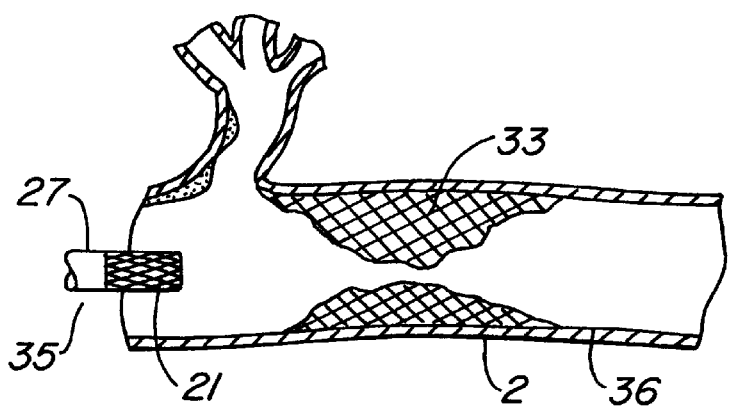
FIG. 9A illustrates the expandable channel PYTHON of the instant invention in its un-deployed state in a tubular channel of the body where it is about to be deployed and engulf an obstruction within the vessel.
Figure 9B:
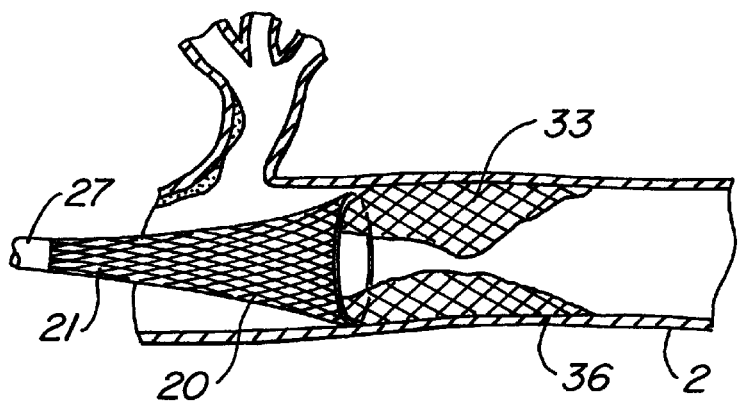
FIG. 9B illustrates the expendable channel, PYTHON, of the instant invention, as it is being deployed and beginning to engulf the obstruction.
Figure 9C:
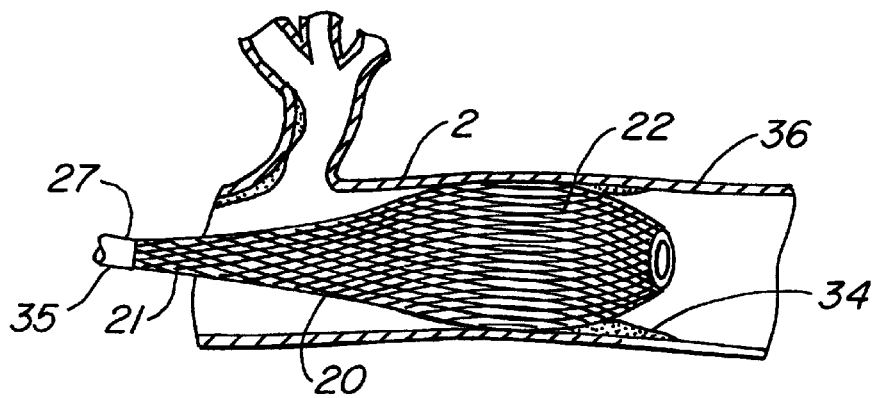
FIG. 9C illustrates the PYTHON expandable channel of the instant invention in its deployed state with the obstruction engulfed within the expanded/deployed channel. Not illustrated is a covering that may be over or within the expandable channel.
Figure 10A:
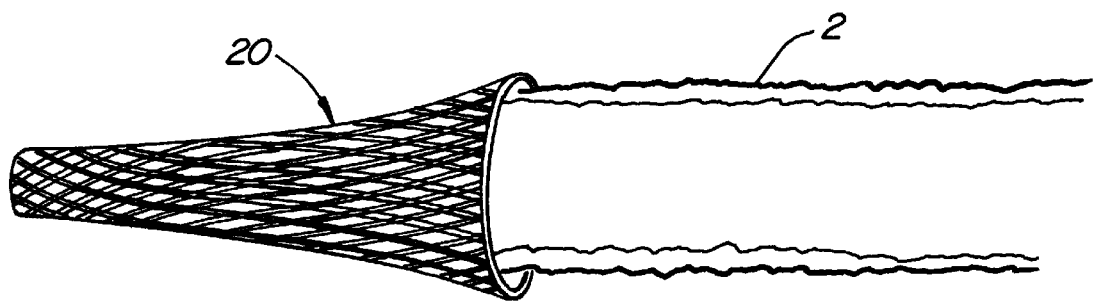
FIGS. 10A and 10B illustrate an expandable channel used to remove a section of a vessel for harvesting purposes.
Figure 10B:
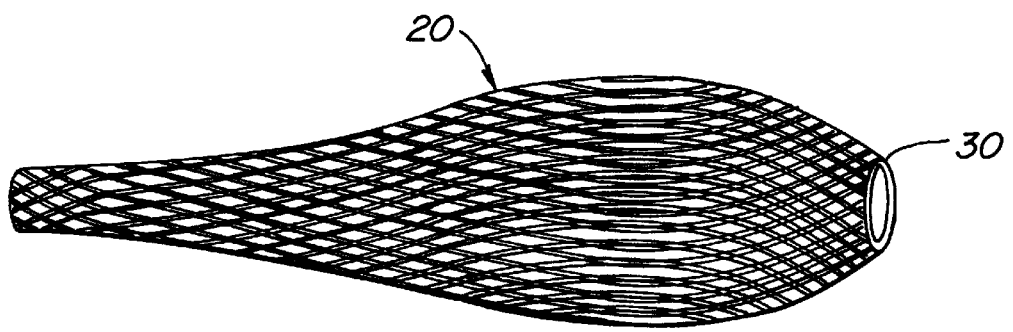

Referring now to FIG. 9, the preferred embodiment of the instant invention is illustrated. FIG. 9A is a cross sectional view of an artery 2 that is diseased with an obstruction 33 which is usually plaque that is deposited onto the inner wall of the vessel. In FIG. 9A, the PYTHON 35 has been advanced into the artery 2 and is just proximal to the occlusion 33. At this point, the PYTHON 21 moved forward relative to the occlusion 33 and shaft 27 and begins to expand 20 in FIG. 9C. Again, the amount of expansion is easily controlled as previous discussed. As the PYTHON 20 is moved forward, it can separate the obstruction 33 from the wall of the artery 2 because there is a natural plane 36 that exists here between the plaque 33 and wall of the artery 2. This separation of the plane is not illustrated in FIG. 9. Instead, the PYTHON 20 separates the obstruction 33 from itself and provides a larger flow lumen in the artery. Also not illustrated is the PYTHON being used in a similar fashion as is illustrated in FIG. 9 except that the PYTHON is used externally to the vessel for harvesting. This is most common for vein harvesting for the physician (vascular surgeon) to use the harvested vein as a graft to replace diseased arteries. The most common harvested vein is the saphenous vein. FIG. 9C illustrates the PYTHON with some of the occlusion entrapped within the PYTHON.

These illustrations show only some potential configurations of the instant invention. Other parametric changes of the instant invention can occur such as location of the trapping element on the distal portion of the device as well as the actual type of mechanism(s) or trapping element used. Additionally, the location of these mechanisms may vary from the proximal to the distal end although all figures illustrate a distal location. Removal of tumors or other diseased tissue from otherwise healthier tissue, removal of foreign objects from channels, cavities or tissue in the body, etc. is also disclosed.

The device of the instant invention is used for intervention into the tubular channels (arteries, veins, biliary tract, urological tract, gastro-intestinal tract, stents, grafts, sinuses, nasopharynx, heart, ears, etc.) or hollow cavities (stomach, gall bladder, urinary bladder, peritoneum, etc.) of the body. Additionally the instant invention may be used in solid or semi-solid tissue including, but not limited to breast, liver, brain, pancreas, lungs etc. It is particularly convenient to use in an operating room, surgical suite, interventional suite, Emergency Room, patient's bedside, etc. environment. One preferred embodiment of this device is that the flexible shaft is inserted into the tissue, tubular channel or hollow cavity of the body usually through pecutaneous access or via a surgical incision. In the case of lumens that enter and exit the body naturally, the device may enter through one of those entry or exit paths (i.e. rectal opening, mouth, ear, etc.). The TRAP pulls the matter proximally toward the PYTHON or holds the matter from moving distally in the case when the PYTHON is moved forward. If used, the TRAP(s) mechanisms is deployed (usually actuated by the physician outside the body) so that the umbrella(s)/trap(s) configuration on the device opens/deploys. As the TRAP is pulling the obstruction toward the PYTHON channel, the PYTHON channel begins to open due to the PYTHON channel being put into compression. Alternatively, the PYTHON can be put into compression by moving it forward which expands the PYTHON around the material. This opening of the PYTHON channel may be aided by creating a slight flare at the most distal end of the PYTHON channel. As the matter enters the PYTHON channel and is enclosed within the PYTHON channel, the distal end of the PYTHON channel may close. Other mechanisms commonly known to anyone normally skilled in the art could be used to enhance the closure of the distal end of the PYTHON if so desired. One such mechanism may be a snare, which is located on the distal end of the PYTHON. In this case the physician might pull on a string or wire that actuates the snare and pulls the PYTHON closed. Further, other mechanisms using electrical, magnetic, mechanical, etc. energies could be used. This closing or compression of the PYTHON channel can be aided by pulling on the PYTHON channel and hence putting it into a tensile mode. The TRAP and the PYTHON channel described herein are usually inserted into the patient in an un-deployed fashion. It may arrive in the package in a deployed or un-deployed state.

Once the device is in the desired position within the body, the umbrella(s)/TRAP(s) like mechanism(s), if used, is deployed. At this point, the user will pull the device in a retrograde fashion into the PYTHON channel and then remove (or dissolve or otherwise obliterate) the matter from the hollow structure. Alternatively as previously stated, if used, the TRAP may be used to keep the matter from moving distally while the PYTHON is moved forward. Sometimes this removal is assisted with suction/aspiration applied to the obstruction proximally (with the TRAP(s) deployed distally). Alternatively, the obstruction could be engulfed inside the PYTHON channel using aspiration/suction. Even further, the obstruction could be engulfed inside the PYTHON channel by merely pushing the PYTHON channel forward toward the obstruction with or without the aid of a TRAP, irrigation, aspiration, suction etc. This forward pushing causes the PYTHON channel to be put into compression which in turn causes the PYTHON channel to open up to the largest diameter. This largest diameter is available either by the design of the PYTHON channel or by the size of the channel/lumen where the matter is located or other tissue constraints. In the case of solid or semi-solid tissue containing diseased tissue or other matter that is desirable to be removed, additional instruments may be used. As one example, the removal of a tumor from the breast may be aided with an obliterating device (mechanical cutting, electrical, sonic, thermal, etc.). In this case, the physician would locate the tumor to be resected or otherwise obliterated usually with the aid of image intensification (x-ray, palpation, mammography, stereotactic x-ray, ultrasound imaging, endoscopes, etc.). An elongate obliterating device may be inserted into the breast to the tumor site where expandable 'blades' would be deployed to a degree equal to the amount of tissue to be removed. Such obliterating blades have been used for removal of tumors in other solid or semi-solid tissue. The blades may be mechanically cutting blades or alternatively, other energy sources may be used to affect the cutting of the tissue. In this case of cutting, once the tissue is severed using the cutter, the PYTHON would be pushed forward toward the severed tissue. The blades would help in expanding the PYTHON around the severed tissue. In this instance it is likely that the PYTHON would be coated with a covering that would not allow the severed, diseased tissue from being in contact with other healthier tissue while it is being removed. This covering may be elastic or inelastic material. Such materials may include but are not limited to silicone rubber, polyurethanes, PET, MYLAR, polyethylenes, etc. This covering may be advantageous for other applications of the PYTHON where the material being removed is desired to be fully encapsulated within the PYTHON tubular braid channel without allowing for any fragmented components to pass through the porous filaments of the braid. Additionally, other techniques may be used for removal assistance such as the use of lytic agents, laser energy, dissolving agents, hydraulic assistance, mechanical agitation, vibration, ultrasonic energy or any other variety of assistance that will aid in the removal. Image intensification (Ultrasound, fluoroscopy, MRI, etc.) may be used as well to help with assuring the technique/removal is successful. Additionally, direct visualization using cameras or endoscopes may be used as well.

Possible configurations of the distal TRAP(s) mechanism(s) are varied. One such mechanism(s) is a balloon that is inflated distally to the obstruction. This technique has been used for several years and has its place. However, because of the usual smoothness that is realized with balloons, the balloon can deform and slide past the obstruction or just not be effective enough to remove enough of the obstruction. Hence, one preferred embodiment of the instant invention uses a texturing on the balloon to help with removal. This texturing can be done by actually creating a rough surface on the outside of the balloon material that is part of the wall of the balloon itself. Usually the balloon material is made of elastic material such as silicone, latex, rubber, urethane, etc. Alternatively it could be formulated with just a flexible, but somewhat inelastic material such as PET, Mylar, Polyester, or any number of other inelastic, but flexible materials. Further, the material could be of some hybrid elastic/inelastic material or compliant material. Even further, the balloon may be aided with some other mechanical substructure that aids in the outward radial force that is created by the balloon. All of these configurations may or may not have a roughened texture on the exterior surface that will aid in the removal of the obstruction. Alternatively, all of the above mentioned configurations could have a separate or additional material applied over the inflatable membrane which may or may not be roughened. The roughened surface on the balloon, malecot, covering or film within the malecot and braided devices is easily accomplished in the manufacturing environment. One such way is to create bubbles in a liquid slurry of the polymer prior to its solid curing. Another might be the addition of dissolvable crystals to the surface of the liquid polymer prior to its cure. These dissolvable crystals could then be removed (washed off) after curing of the polymer.

Another configuration that could be used for the TRAP is a mechanism(s) known as a malecot. This malecot is a common configuration used in catheters for holding them in place (in the case of feeding tubes in the intestines or stomach). It is usually a polymeric tube that has more than one, but usually two or more slits symmetrically opposed. When the distal tip of the malecot is put into compression (usually by pulling an inner wire or mandrel or tube), the sides of the polymer are pushed outward to create a larger diameter on the distal tip. This larger diameter is larger than the body/shaft of the device. In the case of a malecot type configuration (as with the inflatable mechanism(s) mentioned above), the surface of the malecot could be roughened or a separate membrane (attached or not) could be put over or under the malecot so that it is roughened or strengthened. Further, a membrane that connects the ribs or wings of a malecot is easily fabricated to increase the surface area of the malecot ribs or wings alone.

Yet, another alternative design of the TRAP is one that has similarities to the malecot, but uses a multi-stranded braid on the distal end. When the braid is put into compression, the braid is pulled together and it flares out to create a larger diameter on the distal end. Alternatively, either the braid or the malecot can have a permanent set put into in so that it is normally open with the larger diameter. In this case, when it is put into tension (usually from some inner (or outer) core wire or mandrel), it collapses down to the diameter of the shaft of the device.

Alternatively, too much abrasive action on the surface of the mechanism(s) may be deleterious to the patient as well. In the case of the braided configuration, some smoothener may be required so that just the appropriate amount of friction is realized for effective obstruction removal. Further, the realized rigidity of any of the type of mechanism(s)s must be optimized for this removal in the particular application.

The PYTHON channel can also be fabricated from several materials and configurations. One preferred configuration is similar to one of the TRAP designs; that being a multi-stranded braided device. The strands can be made of any material that would be useful for a particular application (polymers like polyester, nylon, Mylar, etc.) or, metal (stainless steel, Nickel Titanium Allow (Nitinol), platinum, etc.). Certainly, the materials of the instant invention are not constrained to those materials listed. Additionally, the PYTHON channel may be coated or encased in an elastomeric or other covering. Further, the PYTHON channel may be fabricated of a material that will enlarge due to different forces than that of the braid mentioned previously. One other such force derived mechanism could be a material that swells/enlarges when put into a moist environment. Another such forced derived mechanism is one that swells/enlarges when thermal energy is applied such as Two Way Shaped Memory Alloy (TWSMA) such as a Nickel-Titanium alloy. Yet, another may be one that occurs from an electrical, magnetic or other mechanical configuration/design/force.

The Tubular Braid Elements

The TRAP apparatus includes an elongate tube; an elongate mandril inside the tube and an expandable tubular braid. The elongate mandril extends from the proximal end of the device to the distal end. The elongate tube usually extends from close to the proximal end of the device to close to the distal end. The distal end of the tubular braid is bonded to the distal end of the inner elongate mandril. The mandril may extend beyond the tubular braid. The proximal end of the tubular braid is bonded to the distal end of the elongate tube.

The braid may be open, but may be laminated or covered with a coating of elastic, generally inelastic, plastic or plastically deformable material, such as silicone rubber, latex, polyethylene, thermoplastic elastomers (such as C-Flex, commercially available from Consolidated Polymer Technology), polyurethane and the like. The assembly of tube, mandril and braid is introduced percutaneously in its radially compressed state. In this state, the outside diameter of the braid is close to the outside diameter of the elongate tube. This diameter is in the range of 10 to 500 mils, and usually 25 to 250 mils (i.e. thousandth of an inch). After insertion, moving the mandrel proximally with respect to the tube expands the tubular braid.

The tubular braid is preferably formed as a mesh of individual non-elastic filaments (called "yarns" in the braiding industry). However, it can have some elastic filaments interwoven to create certain characteristics. The non-elastic yarns can be materials such as polyester, PET, polypropylene, polyamide fiber (Kevlar, DuPont), composite filament wound polymer, extruded polymer tubing (such as Nylon II or Ultem, commercially available from General Electric), stainless steel, Nickel Titanium (Nitinol), or the like so that axial shortening causes radial expansion of the braid. These materials have sufficient strength so that the TRAP element will retain its expanded condition in the lumen of the body while removing the matter therefrom. Further, all expandable mechanisms described heretofore, can be manufactured using shape memory materials so that they are self expanding or even expandable when certain temperatures or thermal energies are delivered to the mechanisms. Such material characteristics can be accomplished with different programming methods such as, but not limited to Two Way Shape Memory (TWSM) alloys.

The braid may be of conventional construction, comprising round filaments, flat or ribbon filaments, square filaments, or the like. Non-round filaments may be advantageous to decrease the axial force required for expansion to create a preferred surface area configuration or to decrease the wall thickness of the tubular braid. The filament width or diameter will typically be from about 0.5 to 50 mils, usually being from about 5 to 20 mils. Suitable braids are commercially available from a variety of commercial suppliers.

The tubular braids are typically formed by a "Maypole" dance of yarn carriers. The braid consists of two systems of yarns alternately passing over and under each other causing a zigzag pattern on the surface. One system of yarns moves helically clockwise with respect to the fabric axis while the other moves helically counter-clockwise. The resulting fabric is a tubular braid. Common applications of tubular braids are lacings, electrical cable covers (i.e. insulation and shielding), "Chinese hand-cuffs" and reinforcements for composites. To form a balanced, torque-free fabric (tubular braid), the structure must contain the same number of yarns in each helical direction. The tubular braid may also be pressed flat to form a double thickness fabric strip. The braid weave used in the tubular braid of the present invention will preferably be of the construction known as "two dimensional, tubular, diamond braid" that has a 1/1 intersection pattern of the yarns which is referred to as the "intersection repeat". Alternatively, a Regular braid with a 2/2 intersection repeat and a Hercules braid with an intersection repeat of 3/3 may be used. In all instances, the helix angle (that being the angle between the axis of the tubular braid and the yarn) will increase as the braid is expanded. Even further, Longitudinal Lay-Ins can be added within the braid yarns and parallel to the axis to aid with stability, improve tensile and compressive properties and modulus of the fabric. When these longitudinal "Lay-In" yarns are elastic in nature, the tubular braid is known as an elastic braid. When the longitudinal yarns are stiff, the fabric is called a rigid braid. Biaxially braided fabrics such as those of the present invention are not dimensionally stable. This is why the braid can be placed into an expanded state from a relaxed state (in the case of putting it into the compressive mode). Alternatively this could be a decreased/reduced (braid diameter decreases) state when put into tension from the relaxed state. When put into tension (or compression for that matter) the braid eventually reaches a state wherein the diameter will decrease no more. This is called the "Jammed State". On a stress strain curve, this corresponds to increase modulus. Much of the engineering analyses concerning braids are calculated using the "Jammed State" of the structure/braid. These calculations help one skilled in the art to design a braid with particular desired characteristics. Further, material characteristics are tensile strength, stiffness and Young's modulus. In most instances, varying the material characteristics will vary the force with which the expanded condition of the tubular can exert radially. Even further, the friction between the individual yarns has an effect on the force required to compress and un-compress the tubular braid. For the present invention, friction should be relatively low for a chosen yarn so that the user will have little trouble deploying the engaging element. This is particularly important when the engaging element is located a significant distance from the user. Such is the case when the percutaneous entry is the groin (Femoral Artery for vascular interventions) and the point of engaging the engaging element is some distance away (i.e. the Carotid Artery in the neck). Similarly, this is true for long distances that are not vascular or percutaneous applications.

Other Comments

An important consideration of the invention described herein is that the support wire with its expanding element can be fabricated with a very small diameter. This is important because it allows an optimally large annular space between the wire and the inside of the PYTHON for maximum obstruction removal. Previous engaging elements have been used that use a balloon for the engaging element. This balloon design requires a larger shaft diameter than that of the present invention. Hence, in these previous devices the annular space is not maximized as in the present invention. The term wire is used to refer to the support portion of the removal TRAP device. The material of the wire need not necessarily be metal. Further, it may be desirable to use a 'double' engaging element (i.e. two braided or malecot expanding elements separated a distance appropriate to entrap the occlusion) in the case for example where the occlusion is desired to be trapped in the vessel. The term wire is used herein to refer to a dual element device having a shell component and a core or mandril component which are longitudinally moveable relative to one another so as to be able to place the braided TRAP element into its small diameter insertion state and its large diameter occlusion removal state.

Additionally, other instruments/mechanisms may be used to help orient the obstruction or tissue into the PYTHON channel. This may be of particular importance when the PYTHON is used in a hollow cavity such as the stomach or peritoneal cavity. In such an instance, a variety of devices (or no devices) may be used to aid with arranging the obstruction, tissue, organ, etc. into the PYTHON.

Device Testing

Prototypes of the PYTHON were fabricated from the materials disclosed heretofore and of the dimensions commensurate with this disclosure. Congealed matter such as blood and gels were installed in graft material (Expanded PTFE) and other polymeric tubular channels (with and without TRAP mechanisms). The PYTHON easily removed more than 95% of the enclosed matter from the graft. Further, metallic tubular braid severed semi-solid material by forcing in into the semi-solid material. This severing of material was accomplished even without the aid of other energies disclosed heretofore.

An exemplary device has the following characteristics:

working Length
  10–500 cm
Working Diameter
  The wire of the TRAP has an outer diameter that ranges from 0.006" to 0.150", but can extend to smaller and larger sizes as technology and procedures require. The TRAP of the instant invention would be small in its un-deployed state (similar to that of the wire mentioned above), but would be expandable to diameters of 10 mils to 500 mils or even larger. The PYTHON channel will usually have two diameters as well, a smaller diameter for insertion into the body which would in the range of 20 to 100 mils or even larger. Moreover, the used or deployed state of the PYTHON channel may extend from 50 mils to 2000 mils or even larger.

Physical Configuration

The device of the instant invention may have conventional lubricious coatings to enhance introduction into the target body lumen, e.g. hyaluronic or other equivalent coatings. Further, the technician may apply a lubricious coating just before surgery. As an advantage of the instant invention, the device will be less difficult to feed it to the desired location in the body due to its decreased size. Another advantage of the instant invention would be the ease with which matter can be entrapped for removal or obliteration. This decreased difficulty will decrease cost due to time in the Operating Room (Operating Rooms costs are estimated in excess of $90 dollars per minute in the U.S.) Additionally, there will be realized a decrease in difficulty for removal of the matter and will aid in patient care/recovery and the potential in deleterious effects due to the inability to remove the matter (part or all) from the patient.

An exemplary device having an umbrella(s)/TRAP(s) mechanism(s) located on its distal tip is illustrated in figures. This TRAP(s) mechanism(s) may be at the tip or somewhere else in the distal portion of the device or even in the middle of the device. Additionally, this mechanism(s) may be any of a number of mechanisms that will help aid in removing the matter.

The pushability of the PYTHON channel or sheath may be limiting and advancement may be problematic. If this should occur, an outer sleeve may be added to the PYTHON channel to aid with positioning of the device in the preferred location (usually adjacent to the obstruction). Once the PYTHON channel is in this position, the sleeve could be removed so that additional push or compression will allow the PYTHON channel to expand, open, and hence entrap the obstruction. Alternatively or in addition to the outer containing sleeve of the PYTHON, an inner mandril wire might be used to pull the PYTHON into the desired position in the body.

Although the foregoing invention has been described in some detail by way of illustration and example, for purposes of clarity of understanding, it will be obvious that certain changes and modifications may be practiced within the scope of the appended claims.

What is claimed is:

1. A device for removal of material from a body, comprising:
    an elongate shaft for insertion into a body, said shaft having a distal end;
    an expandable channel mechanism on the distal end of said shaft, said expandable channel mechanism having a radially compressed state for insertion into the body and a radially expanded state extending near to the diameter of the material to be removed near the distal end of said shaft;
    a support wire that fits through said shaft, said wire having a distal end; and
    a material trap element supported on said distal end of said wire, said trap element having a radially compressed state for insertion of said wire into the body and through or around whatever material is to be engaged and a radially expanded state to engage the material;
    wherein at least a portion of said expanded trap element is positionable distally of the material to be removed and at least one of said expandable channel mechanism and said expanded trap element may be subsequently moved towards the other to entrap said material to be removed;
    wherein said expandable channel mechanism is an annular braided segment, and said trap element is a multi-wing malecot style mechanism, the multi-wing malecot mechanism comprising;
        a tubular member having a distal end; and
        at least two longitudinal slitted sections formed circumferentially on the tubular member, wherein the slitted sections are splayed radially in the expanded state to define wings.

2. The removal device of claim 1, wherein said multi-wing malecot mechanism has a roughened surface.

3. The removal device of claim 1, wherein said multi-wing malecot mechanism has a membrane between said wings to increase surface area.

4. A device for removal of material from a body, comprising:
    an elongate shaft for insertion into a body, said shaft having a distal end;
    an expandable channel mechanism on the distal end of said shaft, said expandable channel mechanism having a radially compressed state for insertion into the body and a radially expanded state extending near to the diameter of the material to be removed near the distal end of said shaft;
    a support wire that fits through said shaft, said wire having a distal end; and
    a material trap element supported on said distal end of said wire, said trap element having a radially compressed state for insertion of said wire into the body and through or around whatever material is to be engaged and a radially expanded state to engage the material;
    wherein said expanded trap element is positionable distally of the material to be removed and at least one of said expandable channel mechanism and said expanded trap element may be subsequently moved towards the other to entrap said material to be removed;
    wherein said expandable channel mechanism is an annular braided segment, and said trap element is an annular braided segment.

5. The device according to claim 1, wherein the annular braided segment comprises a distal end and a closing element at said distal end.

6. The device according to claim 4, wherein the annular braided segment of said expandable channel mechanism comprises a distal end and a closing element at said distal end.

7. A device for percutaneous removal of target material from a breast, comprising:
    a hollow shaft for insertion into a body, said shaft having a distal end;
    an expandable channel mechanism on the distal end of said shaft, said expandable channel mechanism movable between a radially compressed state for insertion into the body and a radially expanded state;
    a support element situated within said shaft, said support element having a distal end; and
    a material trap element supported on said distal end of said support element, said trap element having a radially compressed state, for insertion of said trap element into the body and past a target site, and a radially expanded state;
    a severing device comprising at least one severing element extendable outwardly from the support element so to permit at least a portion of tissue at the target material site to be severed from surrounding tissue.

8. The removal device of claim 7, wherein the severing element is energized to aid movement of the severing device through tissue when moving to said radially expanded state and help prevent seeding of cancerous tissue by such movement.

* * * * *